United States Patent [19]

Bittner

[11] 4,426,741
[45] Jan. 24, 1984

[54] INTRAOCULAR LENS WITH ROTATABLE APPENDAGE

[75] Inventor: Timothy Bittner, Duarte, Calif.

[73] Assignee: Ioptex Inc., Azusa, Calif.

[21] Appl. No.: 366,583

[22] Filed: Apr. 8, 1982

[51] Int. Cl.³ .............................. A61F 1/16; A61F 1/24
[52] U.S. Cl. .................................................. 3/13
[58] Field of Search .................................. 3/13, 1

[56] References Cited

U.S. PATENT DOCUMENTS

| | | | |
|---|---|---|---|
| 3,913,148 | 10/1975 | Potthast | 3/13 |
| 3,975,779 | 8/1976 | Richards et al. | 3/13 |
| 4,257,130 | 3/1981 | Bayers | 3/13 |
| 4,262,370 | 4/1981 | Hartstein | 3/13 |

FOREIGN PATENT DOCUMENTS 32835  7/1981  European Pat. Off. .................. 3/13

OTHER PUBLICATIONS

The Lindstrom Centrex Style 20 Posterior Chamber Lens, (Advertisement), Surgidev Corporation, Santa Barbara, Calif., 4 pp., Jan. 4, 1981.

Primary Examiner—Ronald L. Frinks
Attorney, Agent, or Firm—Theodore J. Bielen, Jr.

[57] ABSTRACT

An intraocular lens having an optical portion with at least one appendage associated with the same. The appendage includes a first portion and a connected second portion. The first portion of the appendage rotates in relation to the optical portion upon the application of an actuating force on the second portion of the appendage.

20 Claims, 8 Drawing Figures

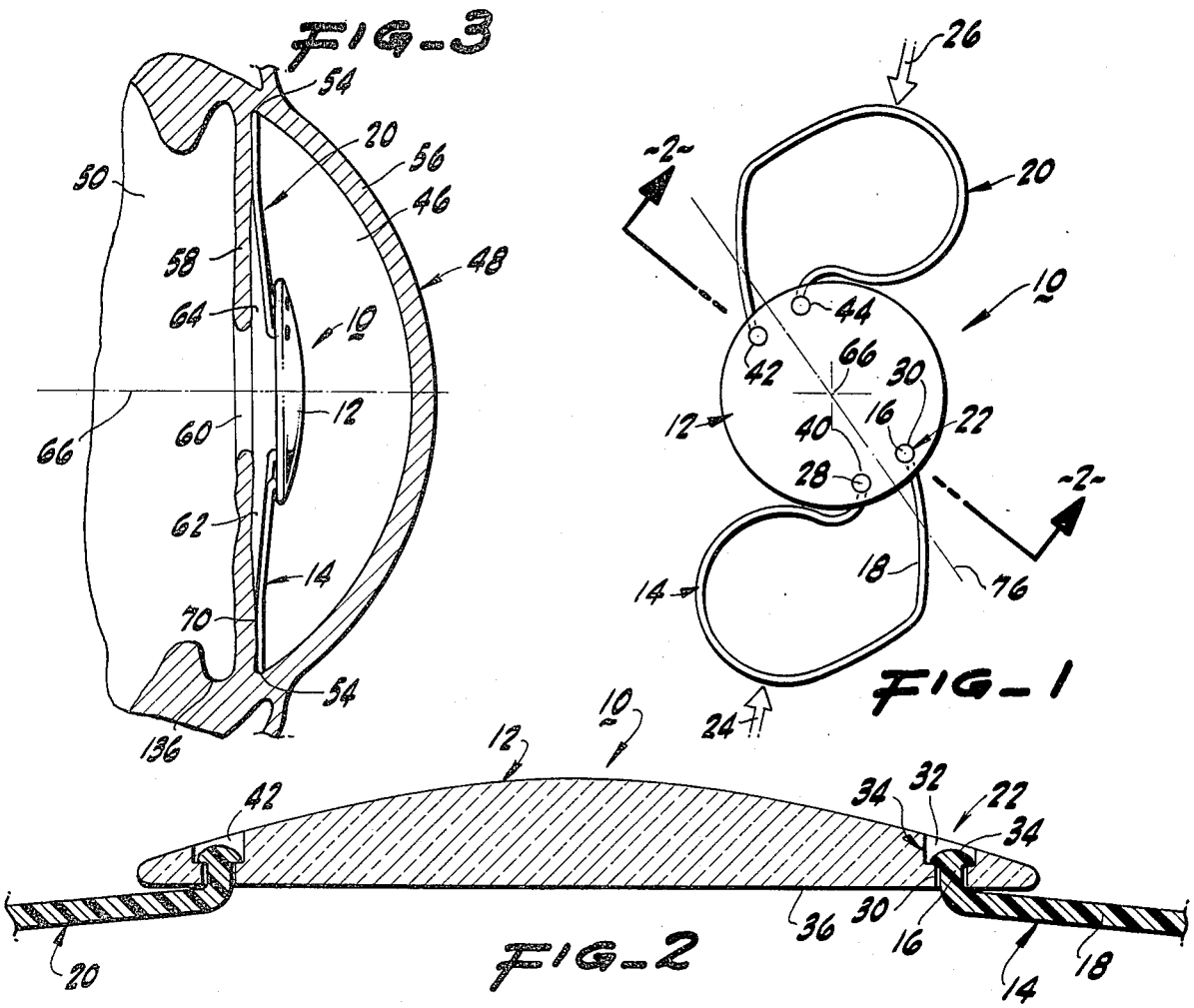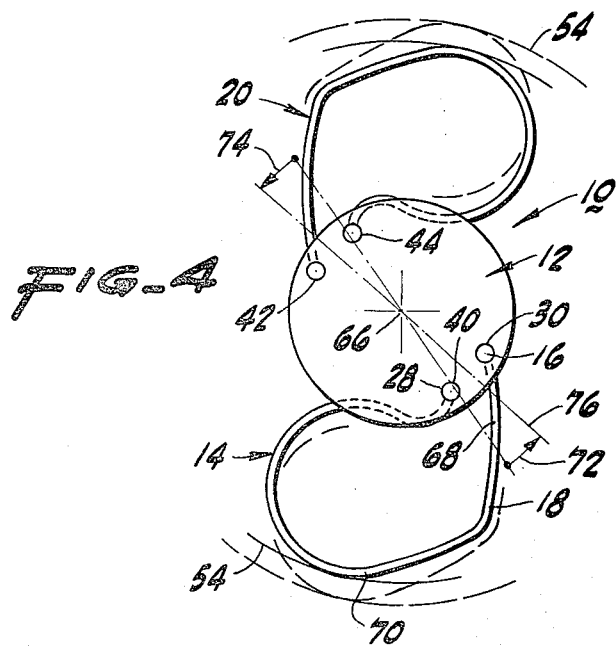

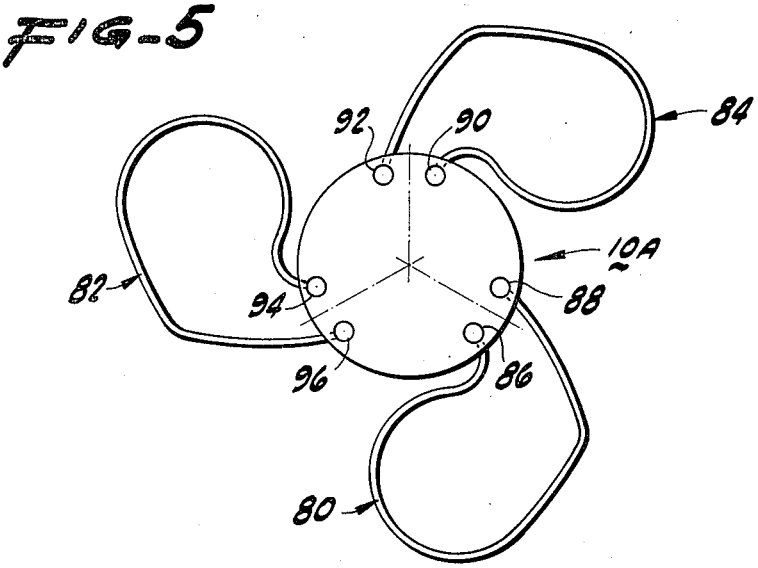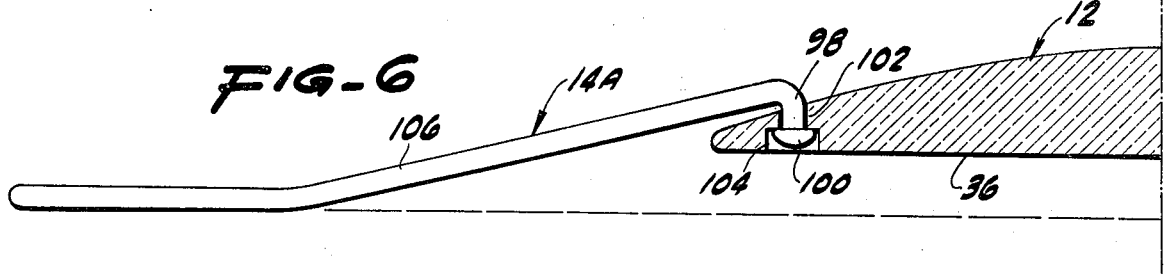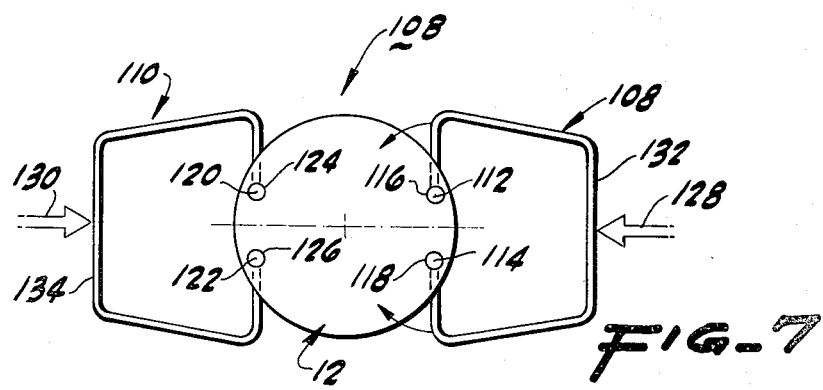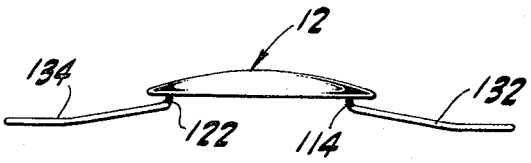

INTRAOCULAR LENS WITH ROTATABLE APPENDAGE

BACKGROUND OF THE INVENTION

The present invention relates to an intraocular lens which may be implanted in the anterior or posterior chamber of the eye after removal of the natural lens of an eye as a result of a cataract condition.

Intraocular lenses have been successfully used to correct impaired vision after cataract surgery. A persistent problem has been the proper fitting of intraocular lenses, thus obviating the necessity of reentry into the eye and replacement of the lens. Also, dislocation of the intraocular lens after placement has caused problems in destruction of endothelial cells, infliction of pain, resulting in reentry into the eye to relocate the errant lens.

Though there is general agreement that posterior chamber placement of intraocular lenses produces an optically superior result, anterior chamber lens is a fairly common procedure. It is believed that placement of an intraocular lens in the anterior chamber of the eye may be accomplished by a less demanding surgical effort. Also, the optical results from an intraocular lens placed in the anterior chamber has been found to be satisfactory. However, there is a distinct danger of destruction of the endothelium layer of the cornea as a result of touching of the same. This touching may occur during the surgical insertion of the intraocular lens or if the intraocular lens in the anterior chamber dislocates or moves forward with changes in the shape of the eye. It has recently been found that it is best for an intraocular lens to not touch the iris portion of the eye in the vicinity of the pupil. For example, U.S. Pat. No. 3,994,027 to Jensen, et al, described a vaulted intraocular lens. Vaulting and adjustability of the fixation mechanism of an intraocular lens has also been found to be useful in the posterior chamber of the eye to avoid touching the iris and to insure that dislocation of the intraocular lens does not occur when the lens is being supported by the ciliary sulcus.

Various designs for flexible or adjustable intraocular lens fixation mechanisms have been proposed. Reference is made to U.S. Pat. No. 4,134,161 to Bayers which shows an intraocular lens mechanism which includes an adjustable leg. The leg may be adjusted before hand or continually adjusted with an elastic spring mechanism. Although this design recognizes the problem associated with the changing dimension of an eye during and after surgery, its use is impractical. The intraocular lens described in U.S. Pat. No. 4,159,546 to Shearing reveals an intraocular lens having springy open looped legs. Although adjustable to a certain extent, the intraocular lens shown therein would dislocate or thrust forward in the anterior chamber causing the problems heretofore described. The same would be true of the lens design shown in U.S. Pat. No. 4,257,130 to Bayers which describes a ribbon loop design. Finally, U.S. Pat. No. 4,296,501 to Kellman describes a hinged leg which determines the overall length of the lens prior to insertion within the eye. Although solving the problem of maintaining a large inventory of lenses, the Kellman lens fails to continually adjust its overall length without movement along the optical axis toward the endothelium layer or the iris in the anterior chamber or toward the iris or vitreous humor in the posterior chamber of the eye (intra capsular surgical procedure).

An intraocular lens which may be placed either in the anterior or posterior chamber of the eye that is adjustable in its overall dimension without thrusting generally at right angles to the deformation force applied would be a very useful advance in the art of manufacture of intraocular lenses and treatment of eye diseases.

SUMMARY OF THE INVENTION

In accordance with the present invention a novel and useful intraocular lens with a rotatable appendage which solves many of the heretofore described problems in the prior art is provided.

The intraocular lens of the present invention utilizes an optical portion with or without a haptic with the proper optical correction determined by prior art methods. At least one appendage is associated with the optical portion by a rotatable connection. The appendage includes at least a first portion and a connected second portion. Means is also provided for permitting rotation in one direction of the first portion of the appendage in relation to the optical portion upon the application of an actuating force on the second portion of the appendage. Rotation in the opposite direction of the first portion of the appendage occurs upon removal of the actuating force.

The appendage may be constructed of flexible material which is nonreactive to biological tissue. The intraocular lens of the present invention may also embrace the addition of a third portion of the appendage which is connected to the second portion and means for permitting rotation of the third portion in relation to the optical portion of the lens. Rotation of the third portion would occur again with application of an actuating force upon the second portion of the appendage which extends away from the optical portion to a distance further than the first or third portions of the appendage. Thus, a closed loop would be formed in this aspect of the invention such that the second portion of the appendage includes a proximal part connected to the first and third portions of the appendage, and a distal part extending from the optical portion to receive the actuating force. The actuating force may be applied by the periphery of the eye during initial placement or upon contraction postoperatively. The distal part of the second portion may be offset from the connection of the first and third portions to the optical portion of the lens to cause rotation of the first and third portions in the same direction relative to the optical portion upon the application of the actuating force. Likewise, the distal part of the second portion may be placed such that the actuating force causes rotation of the first and third portions in the opposite direction relative to the optical portion when the actuating force is applied. It should be noted that the relative rotation may actually cause rotation of the optical portion about its axis without a thrust along the optical axis.

The means for permitting rotation of the first or third portions of the appendage may include an enclosure connected to the optical portion or a hole or opening in the optical portion. The first portion of the appendage may freely rotate within the enclosure or opening. In addition, means is also provided for confining a part of the first portion to the enclosure without preventing rotation of the same within the enclosure. A confining means may include an enlarged portion of the opening as well as an enlargement on the first portion of the appendage. In addition, the second portion of the appendage may be angularly disposed in relation to the first appendage immediately adjacent the lens portion. Such angular connection may include a vaulting configuration described in the prior art.

The intraocular lens herein described may also be constructed with a plurality of appendages to provide multiple point fixation within the chosen chamber of the eye.

The invention provided herein may also be considered to include a method of fixing an appendage to an intraocular lens using the steps of creating an opening in the optical portion with enlargement. The first portion of an appendage is placed in the opening such that the second portion of the appendage remains outside the same. An enlargement is made in the first portion of the appendage within the enlargement portion of the opening such that the enlarged part of the first portion of the appendage cannot pass to the unenlarged portion of the opening. Finally, the second portion is angularly disposed in relation to the first portion immediately adjacent the lens portion. Of course, this angular disposition may provide a vaulting of the lens.

It may be apparent that a novel and useful intraocular lens having a rotatable appendage is provided.

It is therefore an object of the present invention to provide an intraocular lens which has an adjustable overall dimension generally decreasing with the application of a force on the lens appendage and increasing with the removal of such force.

It is another object of the present invention to provide an intraocular lens with an adjustable overall dimension, useable in either the anterior or posterior chamber of the eye which does not thrust along the optical axis when a force is applied to the appendage.

It is yet another object of the present invention to provide an intraocular lens which has at least one vaulted appendage and does not move along its optical axis upon the application of force on the appendage.

It is still another object of the present invention to provide an intraocular lens which may be easily and economically manufactured and may be surgically implanted quickly and safely within an eye.

The invention possesses other objects and advantages especially as concerns particular characteristics and features thereof which will become apparent as the specification continues.

BRIEF DESCRIPTION OF THE DRAWINGS

FIG. 1 is a top plan view of an embodiment of the present invention.

FIG. 2 is a slightly broken sectional view taken along line 2—2 of FIG. 1.

FIG. 3 is a sectional view showing the lens of FIG. 1 within the anterior chamber of an eye.

FIG. 4 is a top plan view of the lens of the FIG. 1 showing the exertion of forces thereupon schematically.

FIG. 5 is a top plan view of another embodiment of the present invention.

FIG. 6 is a broken sectional view of another embodiment of the appendage fixation mechanism of the present invention.

FIG. 7 is a top plan view of another embodiment of the present invention.

FIG. 8 is a side elevational view of the embodiment of the present invention depicted in FIG. 7.

For a better understanding of the invention reference is made to the following detailed description.

DESCRIPTION OF THE PREFERRED EMBODIMENTS

Various aspects of the present invention will evolve from the following detailed description of the preferred embodiments thereof, which should be taken in conjunction with the heretofore described drawings.

With reference to FIG. 1, the invention as a whole is depicted by reference character 10 and includes as one of its elements optical portion 12. Optical portion 12 may be constructed of any known materials which provides the optical correction desired. Optical portion 12 must be nonreactive with human tissue, such as polymethylmethacrylate (PMMA), optical glass, and the like. Although not depicted in the drawings, optical portion 12 may include a haptic to aid in the handling of lens 10.

Connected to optical portion 12 is an appendage 14 which may be constructed of flexible material, such as PMMA, polypropylene, and the like. Appendage 14 includes a first portion 16 angularly connected to second portion 18. With reference to FIGS. 1 and 2, it may be seen that a second appendage 20 is depicted which is constructed similarly to first appendage 14. Returning to first appendage 14, FIGS. 1 and 2, means 22 is also included for permitting rotation of first portion 16 in relation to optical portion 12 upon the application of an actuating force, arrow 24, on second portion 18, FIG. 1. It should be noted that a comparable force, arrow 26, may be placed on second appendage 20 and will be hereinafter described with reference to FIG. 4. As shown in FIG. 1, means 22 rotates first portion 16 in a clockwise direction upon the application of force 24 and in the opposite counterclockwise direction upon the removal of force 24. Second portion 18 may gain purchase from a portion of the eye or optical portion 12 at a place beyond the point of the application of force 24. As depicted in FIG. 1, it may be seen that second portion 18 connects to a third portion 28 which also includes means for permitting rotation similar to means 22.

With reference to FIG. 2, means 22 and the means for permitting rotation of third portion 28, is shown. For the purposes of simplification, it may be assumed that means 22 is identical to the means for permitting the rotation of third portion 28. Means 22 includes a cavity or enclosure 30 having an enlarged portion 32. Enclosure 30 is formed by creating an opening through optical portion 12, but may be formed in other ways such as attaching a bushing or the like to optical portion 12. The first portion 16 also possesses an enlargement 34 which fits within an enlarged opening 32 of cavity 30. Second portion 18 is angularly connected to first portion 16 immediately adjacent the under surface 36 of optical portion 12. Thus, means 38 is provided for confining enlargement 34 to enlarged portion 32 of cavity 30. A second enclosure 40, FIG. 1, is similarly constructed to cavity or enclosure 30. With respect to appendage 20, FIG. 2, enclosures 42 and 44 provide means for rotation of appendage 20 relative to optical portion 12.

Directing attention to FIG. 3, it may be seen that lens 10 is placed in the anterior chamber 46 of eye 48. Lens 10 may also be placed in posterior chamber 50. First appendage 14 and second appendage 20 extend to and contact angle 54 formed by the meeting of cornea 56 and iris 58. It should be noted that appendages 14 and 20 are vaulted or angled away from the portion of the iris adjacent pupil 60 forming gaps 62 and 64 thereby. For the purposes of reference, optical axis 66 is illustrated.

Second portion 18 of first appendage 14 may be deemed to include a proximal part 68 and a distal part 70 extending from the optical portion 12. Proximal part 68 connects to first portion 16 and third portion 28 of first appendage 14. It may be apparent that the proximal part 68 of second portion 14 angularly connects to the first and third portions 16 and 28 of first appendage 14. Distal part 70 is also angularly disposed in relation to proximal part 68 of second portion of first appendage 14. This provision decreases the vaulting angle and the span of gaps 62 and 64 between iris 58 and optical portion 12.

With reference to FIG. 4, it may be seen that distal part 70 of second portion 18 of first appendage 14 contacts the periphery of eye 48, namely angle 54. The comparable part of second appendage 20 also initally contacts angle 54. The position of appendages 14 and 20 in relation to angle 54 are shown in phantom on FIG. 4. After contraction of the overall dimension of the eye as depicted in FIG. 4 or by merely compressing appendages 14 and 20 in which fitting the same within eye 48, once lens 10 takes the configuration shown in solid line format in FIG. 4. As depicted, arrows 72 and 74 show the relative rotation of appendages 14 and 20 in relation to optical portion 12. In actuality, it has been found that optical portion 12 appears to rotate about optical axis 66. It should be noted that distal part 70 of second portion 18 of first appendage 14 is offset from a line 76 between cavities 30 and 40 and cavities 42 and 78 of optical portion 12. Thus, third portion 28 and first portion 16 of appendage 14 rotate in the same direction upon the application of an actuating force on distal part 70 of appendage 14. The complete operation of lens 10 will be described as the specification continues.

With reference to FIG. 5, it is apparent that the lens of the present invention may take another embodiment identified by reference character 10A. Lens 10A includes appendages 80, 82, and 84 rotatably connected to optical portion 12. Again, the distal parts of appendages 80, 82, and 84 offset to produce rotation within cavities or enclosures 86, 88, 90, 92, 94, and 96. Appendages 80, 82, and 84, may be considered identical in construction to appendage 14 hereinabove described. Lens 10A obtains three point fixation in either in the anterior or posterior chamber of the eye. It should also be noted that any plurality of appendages may be affixed to optical portion 12 to obtain more than three point fixation within the limitations of size and the shape of the optical portion and/or the appendages.

FIG. 6 demonstrates a variation of appendage 14 wherein appendage 14A is shown having a first portion 98 having an enlargement 100. A cavity 102 includes an enlarged portion 104 adjacent the under surface 106 of optical portion 12. Thus, the angular connection between first portion 98 and second portion 106 of first appendage 14A is above optical portion 12. Second portion 106 is also depicted as being vaulted to remove optical portion 12 and the bulk of second portion 106 from contact with the pupiliary portion of iris 58.

FIG. 7 depicts another embodiment, lens 10B, of the present invention where a first appendage 108 and a second appendage 110 rotatably connect to optical portion 12. First portion 112 and third portion 114 of appendage 108 are constructed to rotate within cavities 116 and 118. Likewise, first portion 120 and third portion 122 rotate within cavities 124 and 126. The means for permitting rotation of first and third portions 112 and 114 and 124 and 126 of appendages 108 and 110 respectively, would be similar to the construction of first and third portions 16 and 28 of appendage 14, hereinbefore described. An important difference is that force arrows 128 and 130 show second portions 132 and 138 of appendages 108 and 110 rotate the respective first and third portions 16 and 28 in opposite directions. FIG. 8 illustrates the vaulting construction used for the same purposes as the prior embodiments.

In operation, the surgeon would select lens 10, 10A, or 10B having the proper optical correction in optical portion 12. The intraocular lens would be sized slightly larger than the overall dimension of the anterior or posterior chambers 46 or 50 of eye 48. The overall dimension of the lens would be manually compressed and then permitted to expand slightly such that the lens 10 would wedge into the angle 52, 54, or the ciliary sulcus 136 (posterior chamber). The compressing, manually or by contraction of the overall dimension of the eye, would cause rotation of the appendages in relation to the optical portion 12. In general, it has been found that lens portion 12 rotates about optical axis 66 when force is applied at force arrows 24 and 26, FIG. 1. The flexibility of the appendages associated with lens 10, 10A, and/or 10B, would aid in the absorption of forces exerted on the appendages. Release of the force would permit the appendages to return or spring back to their original position.

The invention may also be deemed to include a method of fixing an appendage such as appendage 14 to an intraocular lens utilizing the steps of creating an opening 30 within optical portion 12. The opening 30 would include an enlargement 32. A first portion 16 of appendage 14 will be placed into opening 30 such that the second portion 18 remains outside of opening 30. Enlargement 34 would then be created on the first portion 16 of appendage 14 such that the enlargement fit within the enlarged portion 32 of opening 30. Thus, enlargement 34 would be unable to pass through the remaining unenlarged portion of opening 30. Finally, the second portion 18 would be angularly disposed in relation to first portion 16 of appendage 14 immediately adjacent the undersurface 36 of lens portion 12.

While in the foregoing embodiments of the present invention have been set forth in considerable detail for the purposes of making a complete disclosure of the invention, it will be apparent to those of ordinary skill in the art that numerous changes may be made in such details without departing from the spirit and principles of the invention.

What is claimed is:

1. An intraocular lens comprising:
   a. an optional portion;
   b. at least one appendage connected to said optical portion, said appendage including a first portion, a second portion connected to said first portion, and a third portion linked to said optical portion and said second portion; and
   c. means for permitting rotation in one direction of said first portion of said at least one appendage in relation to said optical portion upon the application of an actuating force upon said second portion of said at least one appendage, and rotation in the opposite direction upon removal of said actuating force.

2. The intraocular lens of claim 1 in which said means for permitting rotation of said first portion of said at least one appendage includes an enclosure connected to said optical portion, said first portion of said at least one appendage being rotatable within said enclosure.

3. The intraocular lens of claim 2 which additionally comprises means for confining a part of said first portion of said at least one appendage to said enclosure.

4. The intraocular lens of claim 3 in which said means for confining at least a part of said first portion of said at least one appendage to said enclosure includes an enlargement on said first portion of said at least one appendage.

5. The intraocular lens of claim 4 in which said means for confining a part of said first portion of said at least one appendage further includes said first portion of said at least one appendage being angularly connected to said second portion of said at least one appendage.

6. The intraocular lens of claim 5 in which said enclosure is a first enclosure and additionally comprises a second enclosure connected to said optical portion, said at least one appendage further including a third portion connected to said second portion of said at least one appendage, said third portion of said at least one appendage being rotatable with the application of an actuating force upon said second portion thereof.

7. The intraocular lens of claim 6 in which said first enclosure comprises a cavity in said optical portion.

8. The intraocular lens of claim 7 in which said second enclosure comprises a cavity in said optical portion.

9. The intraocular lens of claim 1 which further includes a plurality of appendages associated with said optical portion, each appendage including at least a first portion and a connected second portion and means for permitting rotation of said first portion of said at least one appendage in relation to said optical portion upon the application of an actuating force upon said second portion of said each appendage.

10. The intraocular lens of claim 9 in which said means for permitting rotation of said first portion of each of said plurality of appendages includes an enclosure connected to said optical portion, said first portion of each plurality of appendages being rotatable within each of said enclosures.

11. The intraocular lens of claim 10 which additionally comprises means for confining at least a part of said portion of each of said plurality of appendages to said enclosure.

12. The intraocular lens of claim 11 in which said means for confining at least a part of said first portion of each of said plurality of appendages to each of said enclosures includes an enlargement on said first portion of each of said plurality of appendages.

13. The intraocular lens of claim 12 in which said means for confining a part of said first portion of said each of said plurality of appendages further includes said first portion of each of said plurality of appendages being angularly connected to said second portion of said each of said plurality of appendages.

14. The intraocular lens of claim 10 in which said enclosure is a first enclosure and additionally comprises a second enclosure connected to said optical portion and being associated with each of said plurality of appendages further including a third portion connected to said second portion of each of said plurality of appendages and linked to said optical portion, each of said third portions being rotatable with the application of an actuating force upon the said second portion thereof.

15. The intraocular lens of claim 14 in which each of said first and second enclosures comprises a cavity in said optical portion.

16. The intraocular lens of claim 1 in which said third portion connected to said second portion includes means for permitting rotation of said third portion in relation to said optical portion upon the application of an actuating force upon said second portion of said at least one appendage, and rotation in the opposite direction upon removal of said actuating force.

17. The intraocular lens of claim 16 in which said second portion of said at least one appendage includes a proximal part connected to said first and third portions of said at least one appendage, and a distal part extending from said optical portion, said distal part of said second portion being positioned such that application of the actuating force upon the extremity of said distal part in relation to said optical portion, causes rotation of said first and third portions in the same direction.

18. The intraocular lens of claim 16 in which said second portion of said at least one appendage includes a proximal part connected to said first and third portions of said at least one appendage, and a distal part extending from said optical portion, said distal part of said second portion being positioned such that application of the actuating force upon the extremity of said distal part in relation to said optical portion, causes rotation of said first and third portions in the opposite direction.

19. The intraocular lens of claim 1 in which said at least one appendage is a flexible member.

20. A method of fixing an appendage to an intraocular lens comprising the steps of:
   a. creating an opening in an optical portion, said opening having an enlargement thereof within said optical portion;
   b. placing a first portion of said appendage in said opening such that a second portion and connected third portion of said appendage remains outside said opening;
   c. enlarging a part of said first portion of said appendage within said enlargement of said opening in said optical portion such that said enlarged part of said first portion is unable to pass through the unenlarged portion of said opening;
   d. angularly disposing said first portion of said appendage in relation to said second portion of said appendage, immediately adjacent the lens portion and
   e. connecting said third portion of said appendage to said optical portion.

* * * * *